United States Patent [19]

Rosenschein

[11] Patent Number: 5,524,620

[45] Date of Patent: Jun. 11, 1996

[54] ABLATION OF BLOOD THROMBI BY MEANS OF ACOUSTIC ENERGY

[75] Inventor: Uri Rosenschein, Ramat Hasharon, Israel

[73] Assignee: November Technologies Ltd., Yavne, Israel

[21] Appl. No.: 186,639

[22] Filed: Jan. 26, 1994

Related U.S. Application Data

[63] Continuation-in-part of Ser. No. 789,904, Nov. 12, 1991, abandoned.

[51] Int. Cl.⁶ ................................................... A61B 17/22
[52] U.S. Cl. ............................... 128/653.100; 128/660.03; 601/2
[58] Field of Search ................... 601/2–4; 607/97; 606/128; 604/22; 128/660.03, 653.1

[56] References Cited

U.S. PATENT DOCUMENTS

| | | | |
|---|---|---|---|
| 5,158,070 | 10/1992 | Dory | 128/660.03 |
| 5,178,135 | 1/1993 | Uchiyama et al. | 128/660.03 |
| 5,269,291 | 12/1993 | Carter | 601/2 |

*Primary Examiner*—Ruth S. Smith
*Attorney, Agent, or Firm*—Edward Langer

[57] ABSTRACT

A method and device for selective in vivo ablation of fresh blood thrombi by means of non-invasive focused high power acoustic energy. The method comprises applying a plurality of pulses of high energy acoustic waves or a continuous acoustic wave, focused at the location of a thrombus in a blood vessel, resulting in the ablation of the thrombus, and restoration of blood flow. There is also provided a device for the controlled generation and application of focused pulsed, or continuous, acoustic energy waves of predetermined energy and frequency.

10 Claims, 3 Drawing Sheets

ABLATION OF BLOOD THROMBI BY MEANS OF ACOUSTIC ENERGY

This is a continuation-in-part application of application Ser. No. 07/789,904, filed Nov. 12, 1991, abandoned.

FIELD OF THE INVENTION

The invention relates to a novel method for the disintegration of fresh blood thrombi in blood vessels, especially in blood vessels of humans. It further relates to a system for applying high intensity pulsed wave or continuous wave focused acoustic energy to such thrombi, which brings about their disintegration, by cavitation which causes ablation.

Experiments have established that thrombi can be effectively ablated by high energy focused ultrasound, practically no perceivable damage is caused to the blood vessel in which such a thrombus is located. The novel non-invasive application of focused high acoustic energy in pulse wave or in a continuous wave is of considerable advantage over existing procedures for the dissolution or ablation of thrombi which exist today, as all of these are invasive procedures, with their inherent risks.

BACKGROUND OF THE INVENTION

Nowadays thrombus lysis is mainly effected by means of chemical agents, such as tissue plasminogen activator, streptokinase or urokinase which are administered by the IV route. Current results indicate that in the presence of an occlusive clot, these are effective in only about 60 per cent of the cases.

The biological use of focused high-intensity acoustic energy was first studied by Lynn et al., in 1942. They demonstrated that focused acoustic energy can produce deep localized damage at the focal point in various biological tissues in vitro and in vivo, with a minimal effect on the surface and no effect on the intervening tissue.

About 30 years later utilization of focused acoustic energy re-emerged in the biomedical field. Experimental investigation in the use of focused shock waves has led to non-surgical treatment of upper urinary tract calculi. Extensive experience with shock wave lithotripsy has found the method to be safe and highly effective. About 80-90% of the patients with "surgical" calculi were successfully treated, only 7% of the treated patients required intervention to resolve residual problems after shock wave lithotripsy.

The mechanism of shock wave lithotripsy is believed to be associated with the acoustic impedance mismatch between the target calcific calculus (stone) and the surrounding (non-calcific) soft tissue. When the shock waves reach the target, the acoustic impedance mismatch gives rise to pressure changes of magnitudes sufficient for shattering the target calculus. Generally very short, intense pulses generated by a spark gap in a liquid, are used.

The inventor started work in 1985, on harnessing acoustic energy in order to utilize it in interventional cardiology. At the first stage he developed an ultrasound ablation catheter (U.S. Pat. No. 5,163,421). This catheter was a breakthrough in the treatment of coronary artery disease, but it is an invasive procedure which is of course a drawback.

This development was initially met with skepticism by experts in this field as there persisted a general belief that it would not be possible to attain a selective ablation of a thrombus, occluded in an artery, so that the artery would not be damaged. We demonstrated that the arterial wall is very resistant to high energy ultrasound energy. Thrombus is very sensitive to ablation by high energy ultrasound.

Thus, Acoustic energy in interventional cardiology is a "smart energy" which enables the performance of interventional procedures to open up "thrombus-rich" occlusions in arteries with a wide margin of safety. Currently, the ultrasound angioplasty catheter is in the final stages of in vivo evaluation of a coronary prototype.

In 1990 the inventor started to explore the feasibility of non-invasive acoustic ablation of thrombi. A report was published in the American Journal of Cardiology (Rosenschein U, Guberinich D, Yakubov SJ, Bach DS, Abrams GD, Sonda PL, EJ Topol, "Shock Wave Thrombus Ablation: A new method for non-invasive mechanical Thrombolysis". Am J. Cardiol 1992; 70;1358-1361). The objective was to evaluate for the first time the ability of non-invasive acoustic energy to selectively ablate a thrombus embedded within an arterial segment. The purpose of these experiments was to show that there can be effected a selective ablation of the thrombus, essentially without damage to the arterial wall by the acoustic waves. It seems that the focused acoustic wave generates cavitation which depolymerizes fibrin, thus disintegrating the thrombus.

In spite of the fact that such acoustic energy is successfully used with calculi for more than 20 years, no one considered it feasible to use acoustic energy for selective ablation of soft tissue, specifically of thrombi in blood vessels.

SUMMARY OF THE INVENTION

There is provided a novel method for the lysis of occlusive blood clots in mammals, and especially in humans. There is provided a device for carrying out such lysis. The lysis, resulting from an ablative effect of the non-invasive application of pulsed wave, or continuous wave, high-intensity focused acoustic energy, frees the blood vessel of the clot burden and restores blood circulation. The device for use in the invention comprises means for generating high energy focused pulse waves or continuous waves, of acoustic energy, which are applied via intervening tissues, and which are focused onto the thrombus, resulting in its ablation, which is believed to be due to cavitation effect.

Experiments have shown that practically no damage is caused to the blood vessels, which stored the thrombi, during application of ultrasound. The selective controlled ablation of the thrombus can be attained within minutes. The device producing high power focused acoustic energy which converges into the body of the patient, comprises at least one such source of energy. There can be used more than one source, focused onto the same blood clot, so as to apply a plurality of simultaneous or alternating pulses, with less energy passing through intervening tissue for each such pulse train. Continuous wave mode ultrasound waves can also be used.

In the following the invention is illustrated mainly with reference to in vitro experiments. Recent experiments on representive laboratory animals confirm the results of the in vitro experiments and trials with humans are contemplated on the basis of these results. The ablation is advantageously effected on fresh occulsive thrombi, i.e. thrombi which will be less than about 24 hours old, and preferably less than about 6 hours old. Although the application of energy pulses is preferred, the invention also applies to the ablative removal of blood thrombi by means of continuous wave mode ultrasound.

Amongst various possibilities to generate effective acoustic energy pulses there may be mentioned, by way of example, the following:

a. The use of piezoelectric crystals as ultrasound generators. Ultrasound will be in a wide range of frequencies, such as from about 1 KHz to about 5 MHz, with pulses at an energy level which will generally be above that required for a cavitation effect (threshold) at the focus, where the thrombus is located. Pulse duration can be in the millisecond to 1 second range, or it can be a somewhat longer duration. Continuous acoustic waves of suitable frequency can be used.

b. The use of spark type generators which produce shock waves of brief duration, of various frequencies. Energy can be in wide range, preferably in the 10 KV to 50 KV range. The pulse duration will be in the millisecond range, and good results were obtained with pulses of about 1 msec to about 100 msec.

The focusing of the energy can be effected by conventional means, including phased-array, time-array techniques. The acoustic energy generator can be coupled with suitable imaging, such as ultrasound imaging, indicative of the effectivity of the treatment. X-ray imaging can also be used. The number of pulses required depends on a number of parameters. Pulses of adequate energy and frequency are used, and generally from about 20 to 10,000 pulses are required for the adequate ablation of an occlusive thrombus and opening of the blood vessel to unimpeded blood flow. The method of the invention can be used together with the application of a chemical agent for thrombolysis as defined above, and in case of only partial success, such agents can be used subsequently.

The generators of the acoustic waves can be in a wide range of power. Advantageously generators in the range of from about 0.1 W/cm$^2$ to about 100 W/cm$^2$ can be used.

The high power acoustic waves can be applied as continuous waves or as pulses. Advantageously, the acoustic wave generator is operated at 10 KW to about 50 KW in a pulsed manner at a pulse duration of 1 msec to 50 msec at a 1 KHz to about 5 Mhz frequency. The energy density at the focal area is in the range of about 1 W/cm$^2$ to about 20 W/cm$^2$. Advantageously, the acoustic lens of the acoustic generator is positioned at a distance from about 5 cm to about 30 cm from the thrombus, in proximity to the skin of the patient.

There can also be used continuous acoustic waves of suitable power. Such waves can be used for certain periods of time, with a time interval to the subsequent wave.

DESCRIPTION OF THE PREFERRED EMBODIMENT

The invention is illustrated with reference to the following detailed description which is to be contrued in a non-limitative manner. A variety of types of generators of acoustic energy, in pulse wave mode and as continuous wave mode, can be used, the main feature being the application of focused energy of adequate intensity at the focal point to bring about cavitation and the ablation of the thrombus from the blood vessel.

BRIEF DESCRIPTION OF THE FIGURES

The invention is further illustrated with reference to the enclosed schematical drawing and photos, wherein:

As shown in FIG. 1, an experimental setup of a device of the invention, to be used for the ablation of blood thrombi in vitro, comprises in combination an underwater spark gap electrode 1, which generates the required shock-waves. A semi-ellipsoid metal reflector 2, converges the energy to a focal point 3, where the thrombic arterial segment 4 is positioned. There are provided two independent X-ray image conversion systems, comprising X-ray image intensifiers 5 and 5' and X-ray monitors 6 and 6', which make possible to monitor the image of the thrombus during the ablation process. The arterial segment 4 is suspended from a metal frame 7, which can be moved along three spatial axes x, y, z so as to position the thrombus at the focal point 3 of the acoustic energy. An ultrasound imaging system 8, 9 visualizes the arterial segment at the focal point 3.

In vitro experiments.

Human femoral and iliac arteries were obtained during post-mortem examinations. The arterial segments were fixed in 10% neutral formalin for 24 h and then, to preserve arterial elasticity, transferred to a saline solution and kept at 4° C. for less than 7 days. Every 48 h the saline solution was changed.

A fresh thrombus was prepared by filling a 3 mm diameter plastic tube with fresh human blood mixed with thrombin (1 ml blood/20 NIH unit bovine thrombin, T4648, Sigma, St. Louis, Mo.). After 30 min. the thrombus was removed from the plastic tube and dissected to a length approximately one-third that of each arterial segment. The thrombus was weighed and inserted into the artery. The artery was filled with saline, to preclude an artificial acoustic interface between air and fluid (i.e. air bubbles), and ligated at both ends.

Shock waves ablation protocol. A shock wave lithotripter (HM3, Dornier Medical Systems, Marietta, Ga.) was used as source of focused high-power acoustic energy. Underwater high-current electrical spark-gap discharges, with a pulse duration of about 1 msec, generated underwater explosive vaporization of water between the spark-gap electrodes. This generated shock waves in the surrounding fluid which propagate spherically from the site of origin. Positioning the spark-gap electrode in a symmetric hemi-ellipsoid metal reflector focused the shock waves. The reflector reflects and converges the shock waves at a focal point where 90% of the energy are concentrated on a spherical area, approximately 2 cm in diameter. The distance between the spark-gap and focal point is 22.5 cm.

Figure 1:
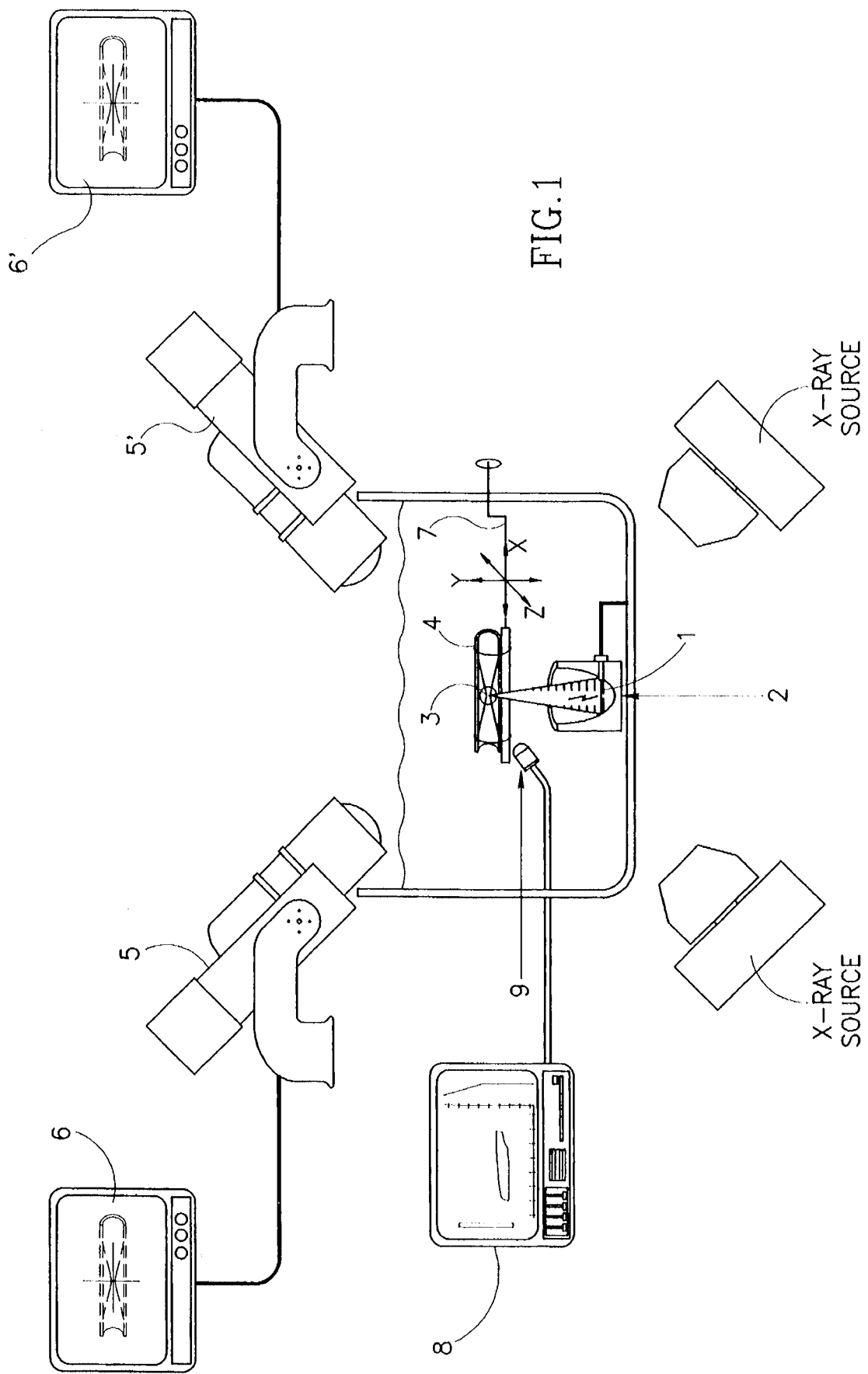
FIG. 1 is a schematic illustration of an in vitro experimental setup.
Figure 3D:
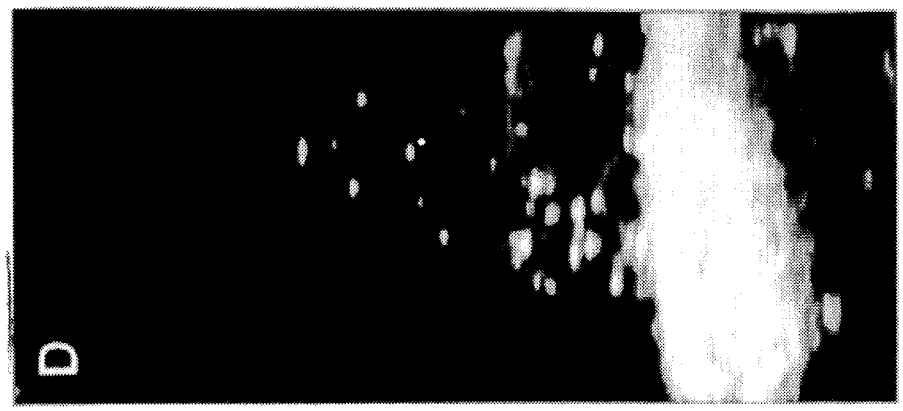
FIGS. 3a to 3d are photos of ultrasound images illustrating the events at the focal point (locus of maximum acoustic energy density) during an experiment of thrombus ablation by means of acoustic energy.
Figure 3C:
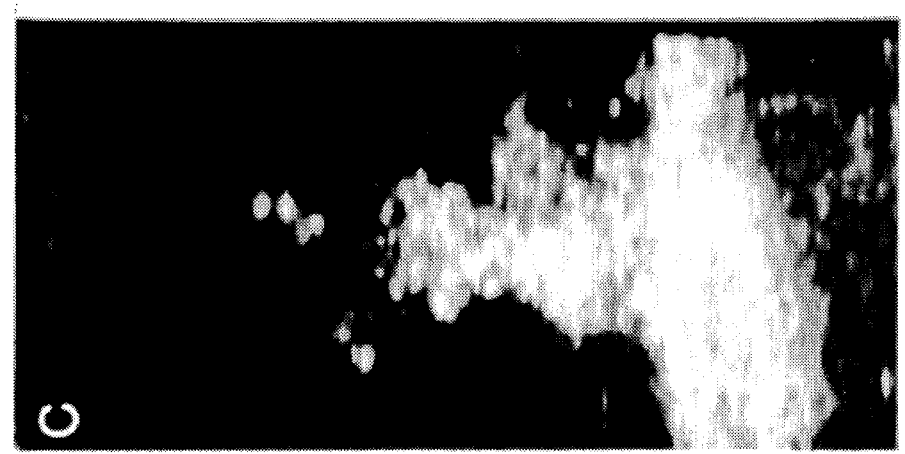
Figure 3B:
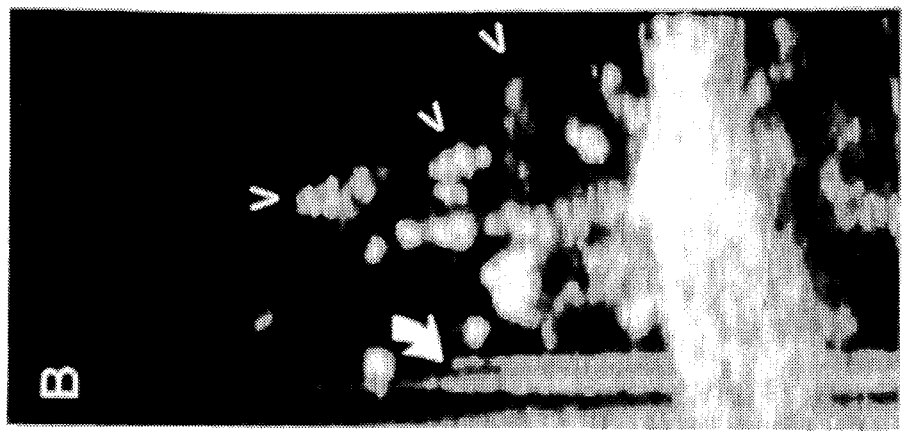
Figure 3A:

The thrombotic arterial segments were randomized into test (n=8) and control groups (n=7). Transillumination confirmed the position of the thrombus in the artery. Radio-opaque markers on both sides of the thrombus identified and defined the thrombotic section during application of shock waves. Each segment was suspended from a metal frame and immersed in a water bath. The water was kept at constant temperature (35°±1° C.). The metal frame with the suspended thrombotic artery could be moved along 3 spatial axes by means of a motor driven positioning device. A X-ray location system, employing 2 independent image conversion systems arranged along nonparallel axes, verified the 3-D positioning of the thrombotic segment at the intersection of the 2 nonparallel axes (i.e. focal point) (FIG. 1). The test arteries were exposed to 1000 shocks at 24 KV. The control arteries underwent identical treatment but without exposure to shock waves.

After the application of shock waves, the arterial ligatures were removed and the arterial content flushed with 10 ml saline. The residual solid thrombus was separated from the fluid portion and re-weighed. The extent of thrombus ablation was evaluated from the change in solid thrombus weight and expressed as percentage reduction in solid thrombus weight. To calculate the percentage reduction in solid thrombus weight the formula: (thrombus weight pre-treatment less thrombus weight post-treatment)×100/thrombus weight pre-treatment, was used.

Figure 2A:
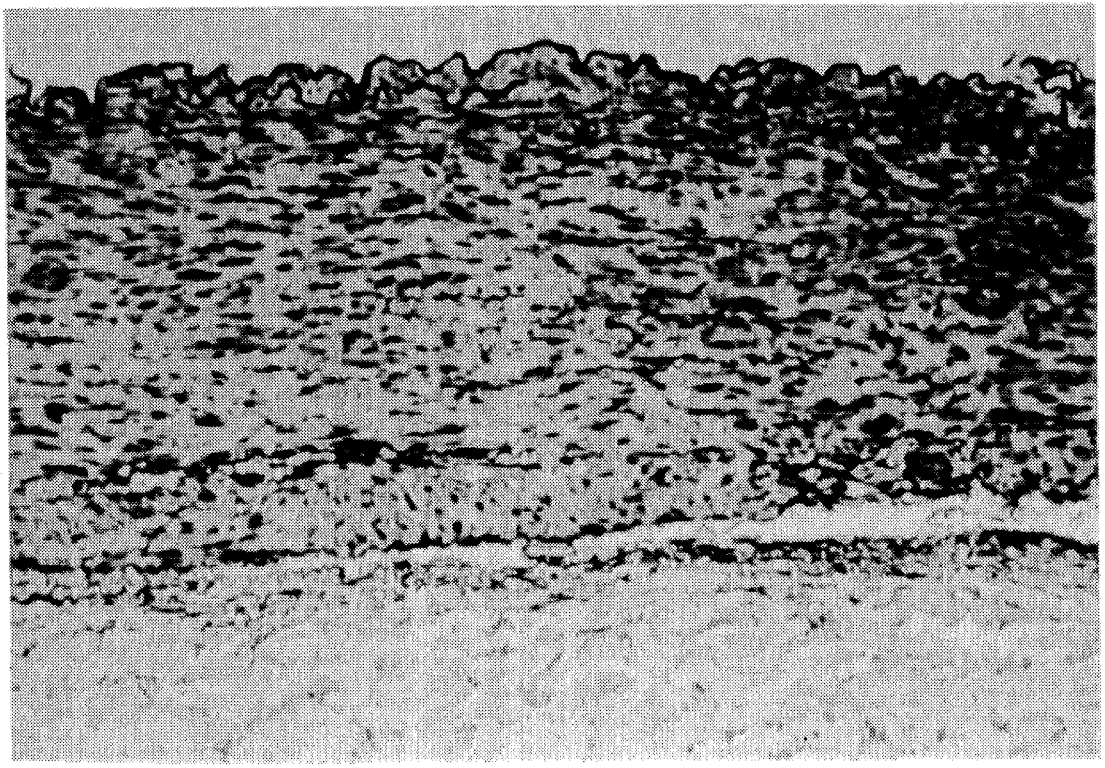
FIG. 2a shows a histological section.
Figure 2B:
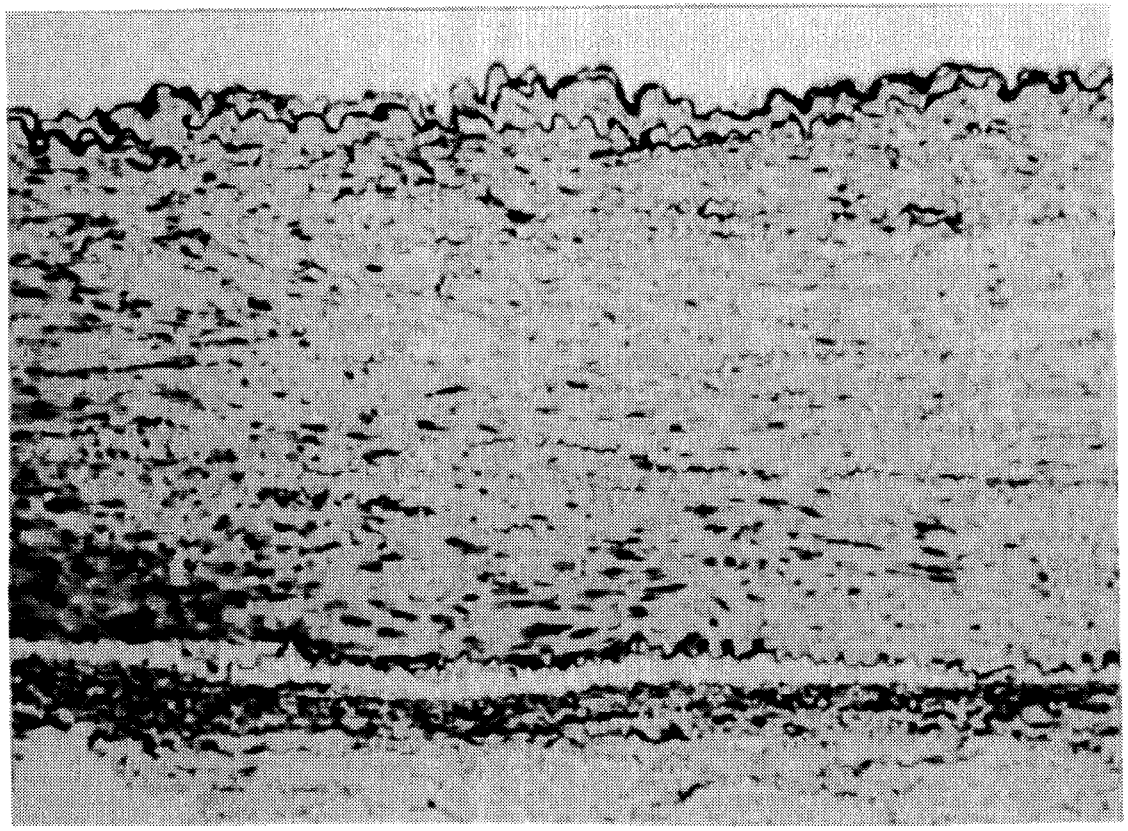
FIG. 2b shows another histological section.

Histopathologic analysis. The arterial segments and thrombi were fixed in 10% neutral formalin. Four 3 mm rings were excised from each segment and processed routinely. Five micron sections, as shown in FIGS. 2a 2b, were mounted on glass slides and stained with Hematoxylin-eosin and Movatpentachrome stains. An experienced cardiovascular pathologist (GDA), blinded to the experimental details and results, performed the pathologic evaluation. The overall integrity of the vessel, Continuity of the elastic structures, and cellular damage was assessed in the arterial segments. The composition and architecture were studied in the thrombi.

Cavitation analysis. To elucidate the mechanism of shock wave thrombus ablation, an ultrasound imaging system was used to study the production of cavitation by the shock waves. The arterial segment was imaged in the water bath before, during, and after each experiment. A 5 MHz multi-element linear-phase array ultrasound imaging transducer, with an axial resolution of 0.3 mm and a lateral resolution of 1.2 mm, at a depth of 4 cm (Ultramark 9, Advanced Technology Laboratories, Inc., Bothell, Wash.), was used. The ultrasound image on display, as shown in FIGS. 3a to 3d, was continuously recorded on a videotape with 240 video-lines of resolution. Cavitations were defined as highly echogenic transient microbubbles on the ultrasound image display. Quadruplicates of the maximal area of each cavitation field were measured and averaged. The time from the spark-gap discharge to the earliest production of cavitation, to attainment of maximal area of the cavitation field and to final clearance of the cavitation was measured in 10 cycles of application of shock waves and averaged. Time was measured by counting the number of video frames from the spark-gap discharge, recorded as electrical interference on the ultrasound image, to the event and multiplying by 33 msec (at frame rate of 30 frames/sec., each frame represents 33 msec). To determine the contribution of acoustic impedance mismatch between the arterial segment and water to the production of cavitation, the echocardiographic studies were performed with and without the presence of an arterial segment at focal point.

Data were summarized as mean ±SD. Differences between groups were analyzed using the unpaired two-tailed Student's-test. A p value <0.05 was considered significant.

Thrombus ablation. The thrombi was generated in vitro, had a diameter of 3 mm, length 3.2±0.4 cm and weight of 0.23±0.08 g. In the test group application of shock waves decreased the weight of solid thrombus weight by 91±14%, as compared with 43±17% in the control group (p=0.0001).

Histopathologic analysis. Following application of shock waves there were no perforations or other gross signs of damage to the arterial segments. No cellular damage was noted in the intima, media, or adventitia. The residual thrombi in both groups were identical in composition and structure.

Cavitation analysis. Shortly after the application of shock waves (533 msec), a localized transient dense field of cavitation was formed at the focal point, the site of maximal energy density, encompassing the thrombotic arterial segment. The field of cavitation attained its maximum dimension (1.9±0.5 $cm^2$). Within 129±62 msec, thereafter it gradually declined in size and density. After 744±233 msec only a few stable cavitations were apparent at the focal point (FIG. 3). The production of cavitation at the focal point after the application of shock waves was characteristic and independent of the presence of an arterial segment of focal point.

This study is the first to show the feasibility of using focused acoustic energy for non-invasive, targeted and selective thrombus ablation. When thrombotic human arterial segments were placed at the focal point of focused shock waves, a 91% reduction in the weight of solid thrombus with no apparent damage to the arterial wall, was observed. In the control group there was a 43% reduction in thrombus weight. This reduction in weight in the control group is attributed mainly to clot-retraction in between the time of thrombus induction and the ablation experiment (12±3 h).

These data, documenting the effective and selective non-invasive thrombus ablation by high-power acoustic energy, are consistent with the data in studies of ultrasonic thrombus ablation by acoustic energy transmitted by a catheter. In these studes, as well, it is shown that the level of acoustic energy necessary to ablate thrombus has a minimal effect on the arterial wall. During ultrasonic angioplasty the ablation rates correlate negatively with elasticity and is apparent only at energy levels above cavitation threshold. The thrombus has a low elasticity and a high ablation rate while the arterial wall has high elasticity and a low ablation rate. This phenomenon of elasticity-dependent ablation by high power acoustic energy is thought to be mediated by cavitation effect and the physical basis for the selective thrombus ablation observed during ultrasonic angioplasty. Thrombus ablation in ultrasonic angioplasty is due to the effect of cavitations. These generate localized disruptive mechanical forces capable of degrading several polymers including fibrin polymer that forms the structural support of the thrombus. Similar mechanism may be operative in shock wave thrombus ablation.

In this study, shock wave effected thrombus ablation, despite the similarities in impendance properties between the fresh thrombus artery, and the surrounding water, suggesting that different mechanism operate here than in lithotripsy. During shock wave thrombus ablation, a localized transient field of cavitation is produced at the focal point encompassing the target thrombotic artery.

Our experiment demonstrate that the mechanism of action is different from that perceived so far to be the mechanism of action of lithoripsy. The mechanism of action of lithotripsy is based on the acoustic impedance mismatch between the soft tissue in the body and the hard calcified stone. This acoustic impedance mismatch generates pressure waves that break the stone apart into very small particles. This explains why lithotripsy, a technology existing for about 20 years, is used only on calcified elements in the body like gallstones and renal stones but nobody had investigated and published on the ablation of soft tissue, specifically on thrombus. Our experiments were extended recently to in vivo experiments in a thrombolytically occluded rabbit's peripheral artery. The occlusion was induced by temporary ligation of the artery and thrombin injection into the occluded segment, as described by Rosenschein et al., (J. Am. College Cardiology 1990; 15: 711–717). The acoustic generator was used to generate a continuous wave, or a pulsed wave with 0.1 second pulse duration, wave frequency 45 KHz, intensity of 5 W/cm² at the focal area which was established to be above the threshold of blood cavitation. In experiments with 5 rabbits such focused acoustic energy ablated the thrombi within 5 to 10 minutes, and led to the restoration of normal blood flow and tissue circulation. A thorough examination of the arteries after thrombus ablation demonstrated no damage to the arteries.

I claim:

1. A method for the non-invasive selective in vivo lysis of blood clots (thrombi) in mammals without damaging blood vessels containing said blood clots, said method comprising the step of applying, by means of an acoustic energy generator, high power focused acoustic energy in a focal area in which said blood vessels containing such thrombus are located, said focused acoustic energy being applied at a level above the cavitation threshold of the blood until the lysis is attained, wherein said acoustic energy generator produces a predetermined ultrasound frequency in the range of about 1 KHz to 5 MHz.

2. A method according to claim 1, wherein said acoustic energy generator produces pulsed waves with a pulse duration in the 1 msec to 1 second range.

3. A method according to claim 1, where the acoustic energy generator produces said ultrasound frequency having an energy density at the focal area between about 0.1 to 100 W/cm².

4. A method according to claim 1, further comprising monitoring the ablation of the thrombus by application of the acoustic energy by X-ray.

5. A method according to claim 1 wherein said ultrasound frequency is produced by a piezoelectric ultrasound acoustic energy generator.

6. A method according to claim 1, further then comprising positioning the acoustic lens of the acoustic generator at a distance from about 5 cm to about 30 cm from the thrombus, in proximity of the skin of the patient.

7. A method according to claim 1, further comprising monitoring the ablation of the thrombus by application of the acoustic energy by ultrasound imaging.

8. A method according to claim 1 wherein said acoustic energy generator produces continuous acoustic waves.

9. A method for the non-invasive selective in vivo lysis of blood clots (thrombi) in mammals without damaging blood vessels containing said blood clots, said method comprising the step of applying, by means of an acoustic energy generator, high power focused acoustic energy in a focal area in which said blood vessels containing such thrombus are located, said focused acoustic energy being applied at a level above the cavitation threshold of the blood until the lysis is attained, wherein said acoustic energy generator produces a shock wave.

10. The method of claim 9 wherein said shock wave is produced by a spark-type acoustic energy generator operating in the range of between 10 KV to 50 KV, with a pulse duration of 1 msec to about 100 msec.

\* \* \* \* \*